United States Patent
Ruffa

(10) Patent No.: US 8,842,497 B1
(45) Date of Patent: Sep. 23, 2014

(54) METHOD AND DEVICE FOR INTERNAL ACOUSTIC MONITORING OF MARINE MAMMALS

(75) Inventor: Anthony A. Ruffa, Hope Valley, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 276 days.

(21) Appl. No.: 13/560,558

(22) Filed: Jul. 27, 2012

(51) Int. Cl.
*H04B 13/02* (2006.01)

(52) U.S. Cl.
USPC .......................................................... 367/131

(58) Field of Classification Search
CPC ....... H04B 13/02; H04B 13/005; A61B 8/546
USPC .......................................................... 367/131
See application file for complete search history.

(56) References Cited

U.S. PATENT DOCUMENTS

2009/0209849 A1* 8/2009 Rowe et al. .................... 600/424
2010/0222670 A1* 9/2010 Demierre et al. ............. 600/424

* cited by examiner

*Primary Examiner* — Daniel Pihulic
(74) *Attorney, Agent, or Firm* — James M. Kasischke; Jean-Paul A. Nasser; Michael P. Stanley

(57) ABSTRACT

The invention is a method directed towards measuring differences in sounds, temperatures and pressures detected within a marine mammal, then analyzing the data to better understand the activities and behavior of the marine mammal. Wherein a buoyant capsule having a hydrophone, a temperature sensor, a pressure sensor, a memory chip, a radio frequency (RF) generator (or other means to enable its detection), software and a battery enclosed within a shell is disposed into a body of water. After a marine mammal ingests the capsule, the capsule is activated after which pressure data and sound data is detected, including sonar transmitted by a monitoring ship. The data is saved on the memory chip for recovery.

14 Claims, 2 Drawing Sheets

METHOD AND DEVICE FOR INTERNAL ACOUSTIC MONITORING OF MARINE MAMMALS

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention is generally directed towards a system and method for monitoring the behavior and activities of a marine mammal in an ocean or other body of water. More specifically, the invention is directed towards measuring differences in sounds, temperatures and pressures detected within a marine mammal, then analyzing the data to better understand the activities and behavior of the marine mammal.

(2) Description of the Prior Art

Many efforts to study marine mammals' response to active sonar have involved tagging the mammals with devices to record the local acoustic field and the depth. However, the tagging operation itself is difficult to do. In a conventional approach, the researchers typically apply a tag externally via a rod to the mammal from a boat. Often only a handful of animals are tagged for a given study.

Capsule endoscopy has been used to record images of the digestive tract of a person in medicine. The capsule is the size and shape of a pill and contains a tiny camera. After a patient swallows the capsule, it takes pictures of the inside of the gastrointestinal tract. The primary use of capsule endoscopy is to examine areas of the small intestine that cannot be seen by other types of endoscopy such as colonoscopy or esophagogastroduodenoscopy (EGD).

SUMMARY OF THE INVENTION

Accordingly, it is an object of the present invention to provide a method and device for monitoring the behavior and activities of a marine mammal in an ocean or other body of water.

The above and other objects and advantages of the present invention will become apparent in view of the following description, claims and drawings.

A method for monitoring behavior and activity of a marine mammal in a body of water, includes the steps of: disposing into the body of water a buoyant capsule having a hydrophone, a temperature sensor, a pressure sensor, a memory chip, a radio frequency (RF) generator, software and a battery enclosed within a shell; inducing the marine mammal to ingest the capsule; detecting temperature changes of the capsule by the temperature sensor; activating the capsule when an internal body temperature of the marine mammal is detected; detecting sound data via the hydrophone, including sonar transmitted by a monitoring ship, and detecting pressure data via the pressure sensor, then saving the sound and pressure data on the memory chip; after excretion by the marine mammal, detecting a water temperature of the body of water to trigger transmission of an RF signal from the excreted capsule, allowing the capsule to be recovered on the surface of the body of water; and retrieving the sound, pressure, and temperature data from the recovered capsule.

A capsule device for monitoring behavior and activity of a marine mammal in a body of water includes electronic components enclosed within a waterproof shell. The capsule is designed to be buoyant in water. The shell is made of material which is harmless to the mammals and will not dissolve in the mammal's digestive track. The capsule includes a temperature sensor, an RF generator, a hydrophone, a battery power source, a pressure sensor, and a memory chip.

DESCRIPTION OF THE PREFERRED EMBODIMENT(S)

This invention provides an efficient monitoring device and process for marine mammals where the mammals are given a pill or capsule 40 (see FIG. 2) that is put into food to encourage the mammal to swallow it. The capsule includes electronics for measuring and recording sounds, temperatures and pressures within the mammal.

Figure 1:
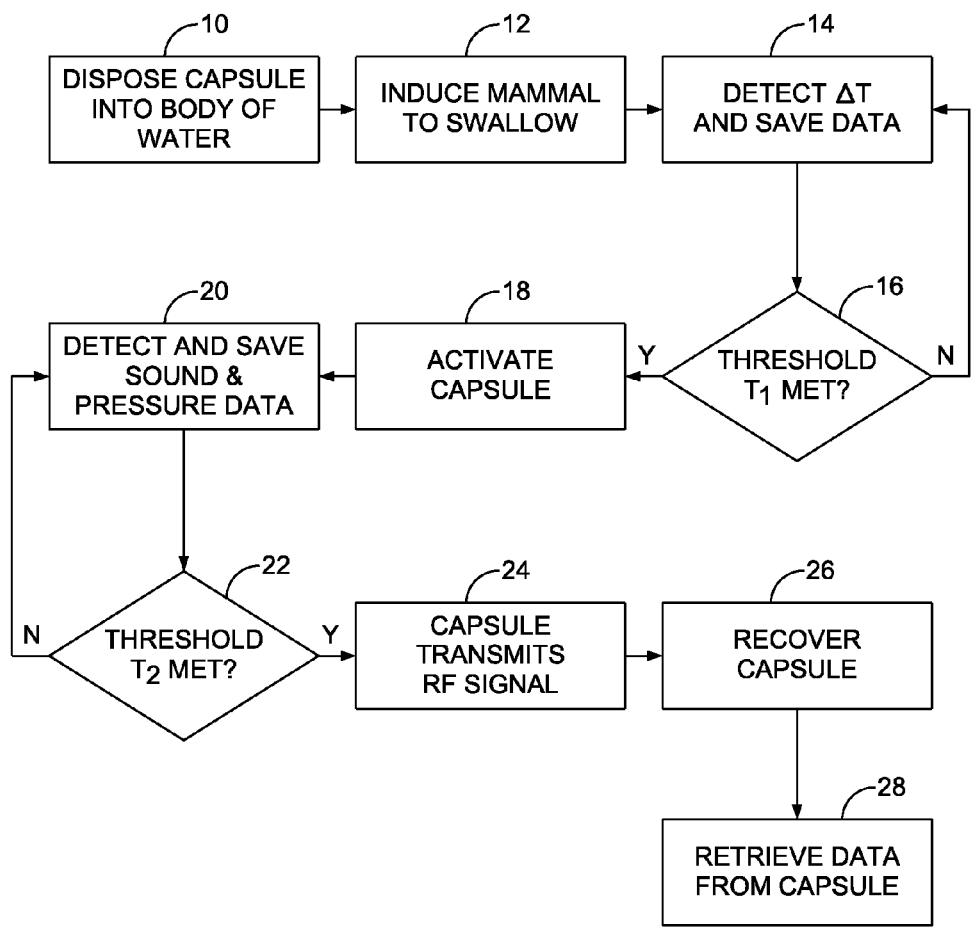
FIG. 1 is a flow diagram of a preferred method of the present invention.

An ocean vessel or ship acts as a base for the monitoring operations. The vessel is capable of transmitting sonar, disposing the capsules into the ocean, and retrieving capsules from the ocean. In step 10 of FIG. 1, the vessel disposes one or more buoyant capsules 40 into the ocean or other body of water where the marine mammals reside, and as indicated in step 12, the mammals are induced to swallow the capsules since they are mixed together with food.

The capsule temperature is constantly monitored by a temperature sensor in steps 14 and 16. While in the water, heat transfer from the water will cause the temperature of the capsule to approach that of the water. After the capsule is ingested by the marine mammal, the capsule temperature will rise to a first threshold of the internal body temperature of the mammal, thus activating the capsule 40 in step 18. When the capsule is activated, the temperature sensor, a pressure sensor, a hydrophone and a memory chip with its associated software all become activated.

The hydrophone determines in step 20 the intensity and presence of sonar and other sound waves within the mammal. For example, sonar transmitted by the monitoring vessel can be measured for intensity within the mammal.

The pressure sensor monitors changes in pressure directly related to the depth of the mammal in the ocean in step 20. Thus the dive patterns of the marine mammal can be determined.

Within a matter of hours the capsule will work its way through the mammal's digestive system and eventually be excreted whereby its buoyancy will cause the capsule to rise to the ocean's surface. Once the capsule is excreted its temperature will decrease from the mammal's internal temperature and approach the water temperature. When the second threshold T2 is met in steps 22 and 24, indicating that the capsule has been excreted back into the water, the RF generator within the capsule will transmit an RF signal which is received by the receiver on the nearby monitoring ship so that the capsule can be recovered in step 26. Note that there are other potential means to detect the capsule as well. For example, the capsule could release oil when it reaches the water surface that could be detected. The oil has the added advantages of not requiring any additional energy for detection, and adding to the buoyancy of the overall capsule design.

After recovery, data within the memory of the capsule is retrieved, for instance, via wireless communication or by any other known means for communications transfer. The data includes temperature, pressure, and acoustic data. Examination of the data provides detailed information about the behavior and activities of the marine mammal. For example, the behavior and sounds emitted by the mammal may be analyzed by marine biologists to reveal potential indications of serenity or distress.

Figure 2:
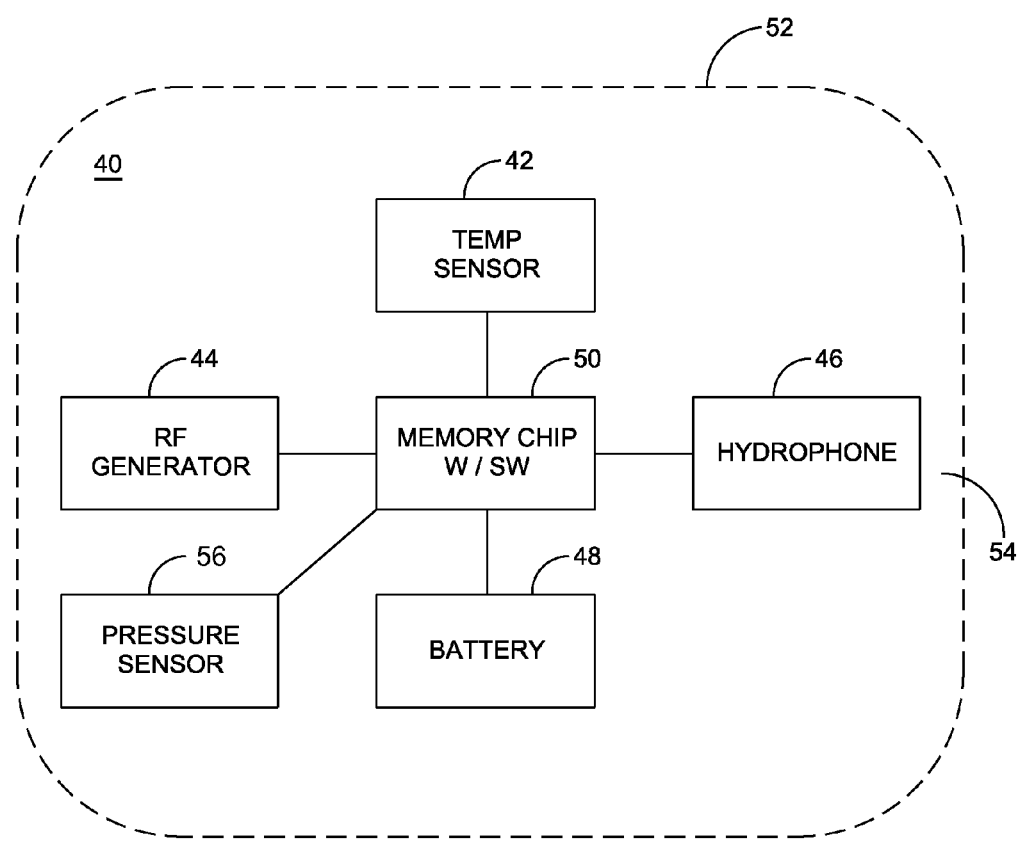
FIG. 2 is a block diagram of a preferred capsule device used in the method of the present invention.

FIG. 2 is a block diagram of a preferred capsule 40 for utilization according to the steps of the marine mammal acoustic monitoring method. The capsule 40 includes electronic components enclosed within an enclosed waterproof shell 52. The shell is made of material (such as silicone or polyurethane), which is harmless to the mammals and will not dissolve in the mammal's digestive track. The capsule is designed to be buoyant in sea water. Within the capsule 40 is a temperature sensor 42, an RF generator 44, a hydrophone 46, a battery power source 48, a pressure sensor 56 and a processor and memory chip 50. No pre-amp is necessary for operation, since monitoring of marine mammals is typically concerned only with high intensity sound waves. Likewise, any vocalizations by the marine mammal will be very loud. Elimination of pre-amps leads to significant energy savings. Each of the components 42, 44, 46, 48 and 56 are connected to the memory chip 50. Also, the hydrophone 46 and the RF generator 44 are surrounded by a liquid 54 such as water which is in contact with the shell 52 to maximize the transmission of sound to the hydrophone.

The hydrophone 46 is an electrical instrument for detecting or monitoring sound underwater including an electro-acoustic transducer that converts sound traveling through water into electrical oscillations. The hydrophone can pick up sounds in the water, from the monitoring vessel, and those produced by the marine mammal that are indicative of the behavior, well being and travels of the mammal.

The pressure sensor 56 measures pressure differences as the mammal dives to different depths in the ocean. The diving patterns of the mammal can also be indicative of the behavior, well being and travels of the mammal.

The temperature sensor 42 is constantly measuring the temperature of the capsule 40. The average temperature of the ocean surface is 17 degrees C. In contrast, most marine mammals have an internal body temperature in the range of thirty four to forty degrees C. Thus after a capsule 40 is ingested by a marine mammal the temperature sensor 42 will detect the change $\Delta T$ in temperature, and when the temperature reaches a first threshold T1 within the internal body temperature range of the mammal, then the capsule 40 will be activated.

Once the capsule 40 is activated, the hydrophone 46, pressure sensor 56, memory chip 50 and its associated software will all become operational to allow the measurement and recording of local acoustic fields, pressures and depths.

This device (in a modified form) can also be useful to law enforcement agencies as an alternative to externally mounted microphone devices (which can be detected much more easily). Having someone swallow a hydrophone capsule would allow recording of their conversation with another nearby person (although perhaps not to the same fidelity as a concealed microphone). However, it would have the advantage that it would be almost undetectable. Such a device will be much simpler than those used for marine mammal monitoring: it does not need to monitor depth, and it does not have to be neutrally buoyant.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A method for monitoring behavior and activity of a marine mammal in a body of water, comprising the steps of:
    disposing into the body of water a buoyant capsule having a hydrophone, a temperature sensor, a pressure sensor, a memory chip, a radio frequency (RF) generator, software, and a battery enclosed within a shell;
    inducing the marine mammal to ingest the capsule;
    detecting temperature changes of the capsule by the temperature sensor;
    activating the capsule electronics when an internal body temperature of the marine mammal is detected;
    detecting sound data via the hydrophone, including sonar transmitted by a monitoring ship, and detecting pressure data via the pressure sensor, then saving the sound data and the pressure data on the memory chip;
    detecting a water temperature of the body of water, after excretion of the capsule by the marine mammal, to trigger a communication means that would allow the capsule to be recovered on the surface of the body of water; and
    retrieving said sound, pressure and temperature data from the recovered capsule via wireless transmission.

2. The method of claim 1, where the communication means allowing the capsule to be recovered comprises transmission of an RF signal from the excreted capsule.

3. The method of claim 1, where the communication means allowing the capsule to be recovered comprises the release of a chemically and visually detectable substance that will float to the water surface, allowing detection of the capsule.

4. The method of claim 1 wherein the shell of the capsule is made of a material which will not dissolve within a digestive system of the marine mammal.

5. The method of claim 1 wherein the hydrophone is immersed in a liquid in contact with the shell of the capsule.

6. The method of claim 1 wherein the marine mammal is induced to ingest the capsule by placing the capsule near or within food appealing to the marine mammal prior to disposal within the body of water.

7. The method of claim 1 wherein the internal body temperature of the marine mammal is in a range of 34 to 40 degrees Celsius.

8. The method of claim 1 wherein the water temperature of the body of water is less than 34 degrees Celsius.

9. An enclosed capsule for monitoring behavior and activity of a marine mammal in a body of water, the capsule comprising:
    a temperature sensor for detecting temperature changes of the capsule and for activating the capsule when an internal body temperature of the marine mammal is detected;
    a hydrophone for detecting sound data including sounds from the marine mammal and sonar transmitted by a monitoring ship;
    a pressure sensor for detecting pressure;
    a radio frequency (RF) generator for transmitting a radio frequency enabling a monitoring vessel to locate the capsule in the water;

a memory chip, including software, for saving the sound data, the pressure data, and the temperature data; and a battery for powering components within the capsule.

10. The enclosed capsule of claim 9, wherein the enclosed capsule is buoyant in water.

11. The enclosed capsule of claim 9 wherein a shell of the capsule is made of a material which will not dissolve within a digestive system of the marine mammal.

12. The enclosed capsule of claim 9 wherein the hydrophone is immersed in a liquid in contact with a shell of the capsule.

13. A method for monitoring a conversation between at least two human beings, comprising the steps of:

having one of the at least two human beings swallow a capsule that houses connected electronics comprising a hydrophone, a programmable memory chip, a radio frequency (RF) generator, and a battery enclosed within a shell which will not dissolve within a digestive system of the human being swallowing the capsule;

activating the capsule electronics powered by the battery;

detecting sounds of a conversation via the hydrophone inside the capsule;

recording the sounds of the conversation on the programmable memory chip that is electrically connected to the hydrophone; and recovering the recorded sounds of the conversation from the memory chip inside the capsule.

14. The method of claim 13 wherein the recorded sounds of the conversation are recovered by transmitting the recorded sounds via the radio frequency generator connected to the programmable memory chip.

* * * * *